US00PP11387P

United States Patent [19]

Kordes

[11] Patent Number: Plant 11,387

[45] Date of Patent: May 23, 2000

[54] FLORIBUNDA ROSE PLANT NAMED 'KOROMTAR'

[75] Inventor: Wilhelm Kordes, Sparrieshoop, Germany

[73] Assignee: Bear Creek Gardens, Inc., Medford, Oreg.

[21] Appl. No.: 09/139,061

[22] Filed: Aug. 24, 1998

[51] Int. Cl.[7] ..... A01H 5/00

[52] U.S. Cl. ..... Plt./145

[58] Field of Search ..... Plt./144, 145, 133, Plt./134

*Primary Examiner*—Howard J. Locker

*Attorney, Agent, or Firm*—Klarquist Sparkman Campbell Leigh & Whinston, LLP

[57] ABSTRACT

Floribunda rose plant having a light yellow flower color; high flower production; excellent vase life; good shipping qualities; and very vigorous growth habit.

1 Drawing Sheet

The present invention relates to a new and distinct variety of rose plant of the floribunda class which was discovered as a single branch spontaneous flower color mutation on a rose plant of the variety 'KORmiller' (U.S. Plant Pat. Application No. 08/985,371, filed Dec. 4, 1997) in a planting of 'KORmiller' in a greenhouse in Sparrieshoop, Germany, which bore a light yellow flower as compared to the pastel pink flowers of 'KORmiller'.

'KORomtar' differs from its parent, 'KORmiller', principally in flower color. It has the same growth, production (26–29 flowers per plant per year in a greenhouse), vase life, good shipping qualities and response to the environment as 'KORmiller'.

Asexual reproduction of this new variety by budding, as performed at Sparrieshoop, Germany, and Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage: Spontaneous mutant of 'KORmiller' (U.S. Plant Patent Application No. 08/985,371, filed Dec. 4, 1997.)

Classification:

*Botanical.*—Rosa hybrida.

*Commercial.*—Floribunda.

FLOWER

Observations made from specimens grown in a greenhouse environment at Sparrieshoop, Germany, and Somis, Calif. from January 1997 to June 1998.

Blooming habit: Continuous.

Bud:

*Size.*—About 1½ inches long when the petals start to unfurl.

*Form.*—Long, pointed ovoid and slightly blunt at the tip.

*Color.*—When sepals first divide, bud color is Yellow Group 4C with Green-Yellow Group 1D on edges of guard petals. When half blown, the upper sides of the petals are Yellow Group 4D on the outer one-third of the petal, Yellow Group 4C on the middle one-third, and Yellow Group 4B on the inner one-third of the petal, and the lower sides of the petals are Yellow Group 4D on the outer two- thirds of the petal and Yellow Group 4C on the inner one-third of the petal.

*Sepal.*—Color: Green Group 138B. Surface texture: Covered in fine hairs. There are three normally appendaged sepals. There are two unappendaged sepals with hairy edges.

*Receptacles.*—Color: Yellow-Green Group 146C. Shape: Funnel. Size: Medium (about 5/16 inch×¼ inch). Surface: Smooth.

*Peduncle.*—Length: Medium, averaging about 2½ inches. Surface: Smooth. Color: Yellow-Green Group 146C. Strength: Stiff, erect.

Bloom:

*Size.*—Medium. Average open diameter is about 3½ to 4 inches.

*Borne.*—Singly and occasionally on new basal shoots several together in pyramidal clusters of five to seven blooms.

*Stems.*—Strong, averaging about 18–22 inches in length.

*Form.*—When first open: High centered. Permanence: Retains its form to the end, outer petals curl back, quill fashion.

*Petalage.*—Number of petals under normal conditions: 25 to 30.

*Color.*—The upper sides of the petals are Yellow Group 4D on the outer one-third of the petal, Yellow Group 4C on the middle one-third, and Yellow Group 4B on the inner one-third of the petal. The reverse sides of the petals are Yellow Group 4D on the outer two-thirds of the petal, and Yellow Group 4C on the inner one-third. The base of the petals has a small, 3/16 inch×3/16 inch Yellow Group 4A half-moon at the point of attachment. The major color on the upper sides is Yellow Group 4D.

*Variegations.*—Occasional greenish streak on the guard petals.

*Discoloration.*—At the end of the first day: No change. At the end of the third day: No change. By day 12–15 in the vase, the upper petal surface fades to Yellow Group 4D across its entire upper surface.

*Fragrance.*—Slight.

Petals:

*Texture.*—Thick, leathery.

*Shape.*—Round.

*Form.*—Tips slightly recurved, edges slightly quilled.

*Arrangement.*—Imbricated. Petaloids in the center are few, small.

*Persistence.*—Petals drop off cleanly before drying.

*Lastingness.*—On the plant: Long (9 to 10 days). As a cut flower: Very long (16 to 18 days).

Reproductive parts:

*Anthers.*—Size: Medium. Quantity: Many. Color: Yellow Orange Group 15A. Arrangement: Regular around styles.

*Filaments.*—Color: Yellow Group 13A.

*Pollen.*—Color: Gold-yellow.

*Styles.*—Color: Greyed-Purple Group 187D.

*Stigmas.*—Color: Greenish-white.

Plant:

*Form.*—Bush.

*Growth.*—Very vigorous; upright; branching. Mature plant, six months after planting, is 5½ feet in height and 3½ feet in width. Plants are maintained at this size by harvesting flowers.

Foliage: Number of leaflets on normal mid-stem leaves: Five.

*Size.*—Large (6½ inches long×4¾ inches wide).

*Quantity.*—Abundant.

*Color.*—New foliage: Upper side and lower sides: Greyed-Purple Group 184B. Old foliage: Upper side: Green Group 139A. Lower side: Green Group 137C. The foliage upper surface will keep the Greyed-Purple Group 184A for several days before becoming green.

Leaflets:

*Shape.*—Pointed oval.

*Texture.*—Leathery. Surface: Matte.

*Edge.*—Serrated.

*Serration.*—Single, small.

*Petiole Rachis.*—Color: Greyed-Purple Group 187B.

*Petiole Underside.*—Smooth.

*Stipules.*—Medium (⅝"). serrated, bearded.

*Disease Resistance.*—Resistant to mildew under normal growing conditions in a greenhouse. Not tested for resistance to blackspot and rust.

Wood:

*New Wood.*—Color: Greyed-Purple Group 187B. Bark: Smooth.

*Old Wood.*—Color: Green Group 139A. Bark: Smooth.

Prickles:

*Quantity.*—On main canes from base: Few. On laterals from main canes: Few.

*Form.*—Short, hooked slightly downward.

*Color when Young.*—Greyed-Purple Group 187B.

*Color when Mature.*—Near Greyed-Orange Group 174D.

Small prickles:

*Quantity.*—On main stalks: None. On laterals: None.

I claim:

1. A new and distinct variety of rose plant of the floribunda class, as herein shown and described, characterized particularly by its light yellow flower color; high flower production; excellent vase life; good shipping qualities; and very vigorous growth habit.

* * * * *

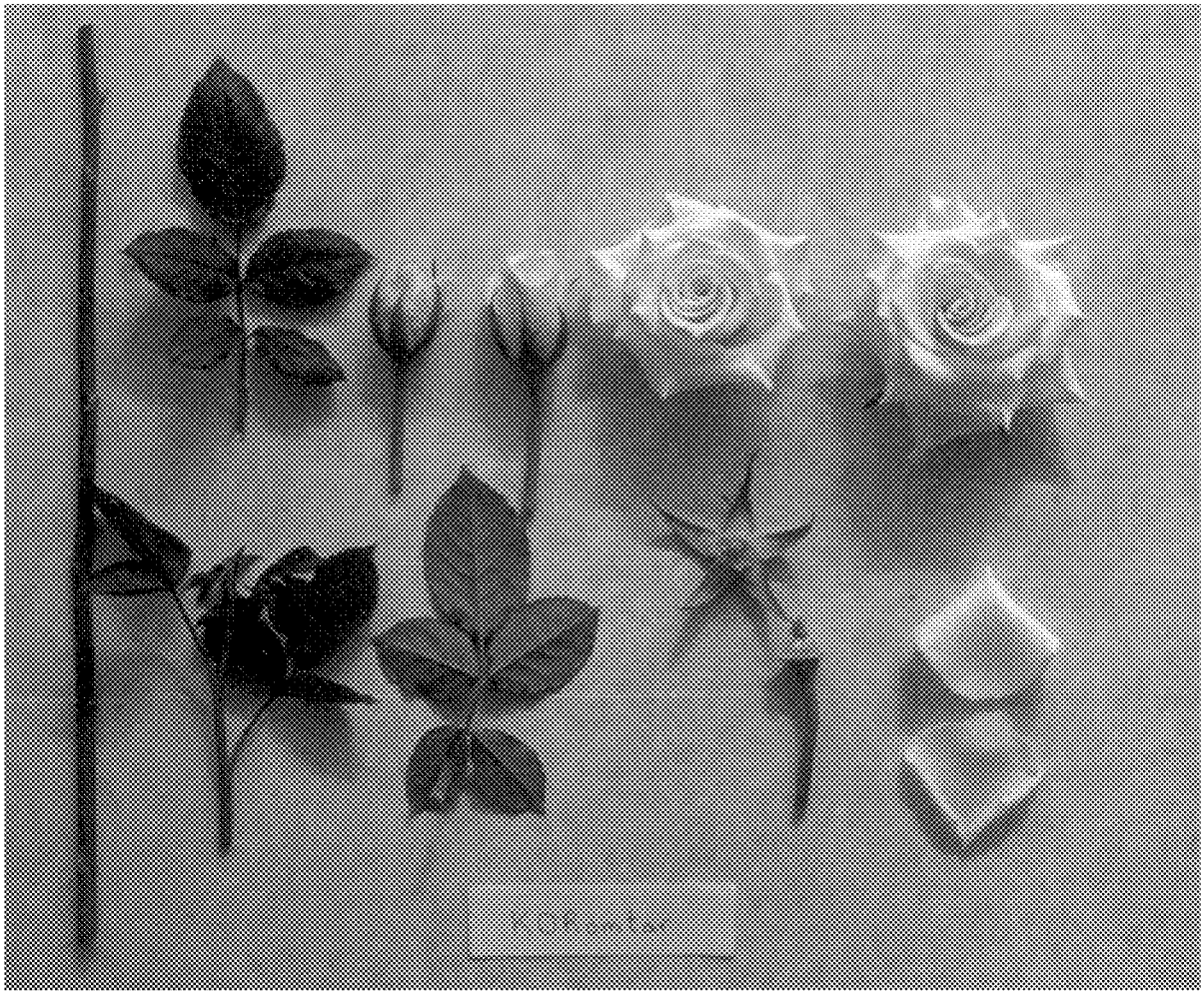

UNITED STATES PATENT AND TRADEMARK OFFICE
CERTIFICATE OF CORRECTION

PATENT NO. : PP11,387

DATED : May 23, 2000

INVENTOR(S) : Wilhelm Kordes

It is certified that errors appear in the above-identified patent and that said Letters Patent is hereby corrected as shown below:

| Col./Line | Error Reads | Should Read |
|---|---|---|
| 3/31 | keep the Greyed-Purple Group 184A for several days before becoming green | rapidly turn green, while the lower surface will keep the Greyed-Purple Group 184B for several days before becoming green. |

Signed and Sealed this

Twenty-ninth Day of May, 2001

*Attest:*

Nicholas P. Godici

NICHOLAS P. GODICI

*Attesting Officer*

*Acting Director of the United States Patent and Trademark Office*